United States Patent
Mihan et al.

(10) Patent No.: US 7,737,230 B2
(45) Date of Patent: Jun. 15, 2010

(54) NMR METHOD OF DETERMINING AND REGULATING THE COMPOSITION OF POLYMER MIXTURES IN POLYMERIZATION

(75) Inventors: Shahram Mihan, Bad Soden (DE); Dieter Lilge, Limburgerhof (DE); Wolfgang Rohde, Speyer (DE)

(73) Assignee: Basell Polyolefine GmbH, Wesseling (DE)

( * ) Notice: Subject to any disclaimer, the term of this patent is extended or adjusted under 35 U.S.C. 154(b) by 464 days.

(21) Appl. No.: 11/629,542

(22) PCT Filed: Jun. 9, 2005

(86) PCT No.: PCT/EP2005/052683

§ 371 (c)(1), (2), (4) Date: Dec. 13, 2006

(87) PCT Pub. No.: WO2005/124324

PCT Pub. Date: Dec. 29, 2005

(65) Prior Publication Data

US 2008/0200622 A1    Aug. 21, 2008

Related U.S. Application Data

(60) Provisional application No. 60/587,522, filed on Jul. 13, 2004.

(30) Foreign Application Priority Data

Jun. 18, 2004    (DE) .................... 10 2004 029 465

(51) Int. Cl.
*C08F 2/00* (2006.01)
*C08F 210/00* (2006.01)

(52) U.S. Cl. ........................ 526/72; 526/348

(58) Field of Classification Search ............... 526/72, 526/348
See application file for complete search history.

(56) References Cited

U.S. PATENT DOCUMENTS

| 6,437,565 B1 | 8/2002 | Early et al. |
| 6,610,799 B1 | 8/2003 | Follestad et al. |

(Continued)

FOREIGN PATENT DOCUMENTS

DE    102004020524    11/2005

(Continued)

OTHER PUBLICATIONS

N. Parizel et al., "N.m.r. and d.s.c. investigation of the miscibility of poly(methyl methacrylate)/poly(ethylene oxide) blends," *Polymer*, vol. 38(15), p. 3719-3725 (1997).

(Continued)

*Primary Examiner*—William K Cheung
(74) *Attorney, Agent, or Firm*—Shao-Hua Guo

(57) ABSTRACT

Method of determining the composition of polymer mixtures comprising defined polymer components of differing mean molar masses $M_n$, which comprises the steps (a) recording of at least one $^1$H-NMR relaxation curve of the polymer mixture and (b) calculating the proportions of the polymer components by matching the measured relaxation curve with the relaxation curves of the individual polymer components.

In this way, the composition of polymer mixtures can be determined quickly and simply. Furthermore, process integration for regulating the polymerization is possible.

18 Claims, 1 Drawing Sheet

U.S. PATENT DOCUMENTS

2004/0058449 A1    3/2004    Early et al.

FOREIGN PATENT DOCUMENTS

| | | |
|---|---|---|
| DE | 102004020525 | 11/2005 |
| EP | 089691 | 9/1983 |
| EP | 475603 | 3/1992 |
| EP | 571826 | 12/1993 |
| JP | 09 071605 | 3/1997 |
| JP | 09071605 A * | 3/1997 |
| WO | 95/08777 | 3/1995 |
| WO | WO 95/08777 * | 3/1995 |
| WO | 96/09328 | 3/1996 |
| WO | 97/04015 | 2/1997 |
| WO | 97/42516 | 11/1997 |
| WO | 00/02929 | 1/2000 |
| WO | 00/50466 | 8/2000 |
| WO | 03/042646 | 5/2003 |
| WO | 2005/103099 | 11/2005 |
| WO | 2005/103100 | 11/2005 |

OTHER PUBLICATIONS

M. Geppi et al., "Dynamics and morphology of polyolefinic elastomers by means of $^{13}$C and $^{1}$H solid-state n.m.r.," *Polymer*, vol. 38(23) pp. 5713-5723 (1997).

* cited by examiner

NMR METHOD OF DETERMINING AND REGULATING THE COMPOSITION OF POLYMER MIXTURES IN POLYMERIZATION

This application is the U.S. national phase of International Application PCT/EP2005/052683, filed Jun. 9, 2005, claiming priority to German Patent Application 102004029465.8 filed Jun. 18, 2004, and the benefit under 35 U.S.C. 119(e) of U.S. Provisional Application No. 60/587,522, filed Jul. 13, 2004; the disclosures of International Application PCT/EP2005/052683, German Patent Application 102004029465.8 and U.S. Provisional Application No. 60/587,522, each as filed, are incorporated herein by reference.

DESCRIPTION

The invention relates to a method of determining the composition of polymer mixtures comprising defined polymer components of differing mean molar masses $M_n$ and to a method of regulating the composition of a polymer in a polymerization reactor in which polymers having differing mean molar masses $M_n$ are prepared sequentially or in parallel by means of at least two polymerization catalysts. It also relates to a polymerization process using this method of regulation.

To produce bimodal and multimodal olefin polymers or polymers of this type having a broadened molar mass distribution, it is traditional to use cascade processes in which polymers of differing mean molar masses are prepared in a plurality of polymerization reactors connected in series. This gives sequentially prepared polymer products which represent mixtures of polymers of differing molar masses.

On the other hand, efforts have been made for some time to prepare bimodal and multimodal products in only one reactor. This can be achieved, firstly, in a multizone reactor as described in WO 97/04015 and WO 00/02929, which is divided into different zones in which different polymerization conditions can be set. As a result, the overall polymer likewise comprises a mixture of polymers having differing structures. For example, if the concentration of a molar mass regulator such as hydrogen is different in the zones, polymer mixtures composed of polymers having differing molar masses can be prepared.

As an alternative, a plurality of catalysts can be present in a reactor under identical polymerization conditions so that polymers having differing molar masses are produced in parallel. This is achieved when a catalyst having a plurality of different catalytically active sites is used. Systems of this type are described, for example, in WO 96/09328.

In all cases, it is important for the production of an in-specification polymer product that information as to whether the product has in-specification properties or the required composition is obtained as early as possible during the production process so that intervention to regulate the process can be carried out promptly.

The composition of the polymer produced is usually determined by gel permeation chromatography (GPC). However, this requires a long measurement time and complicated apparatus, particularly when it is to be combined with the production process. To shorten the measurement time, a rapid GPC with short residence times can be used, but this is at the expense of resolution and therefore leads, particularly in the case of mixtures of polymer components having similar molar masses or broad molar mass distributions, to poor results.

The use of various spectroscopic methods for determining the polymer properties is also known.

WO 03/042646 describes a method of determining polymer properties quickly by Raman spectroscopy for this purpose. The polymer properties can in this case be used for regulating the process in respect of these properties. However, information on the proportion of the various polymer components cannot be obtained here.

On the other hand, WO 00/50466 describes a process for preparing polymers having defined polymer fractions, in which catalyst mixtures of differing compositions are metered independently into the reactor. The various catalysts produce different polymer components. However, precise setting of the proportions of the polymer components requires very precise monitoring of the amounts of catalyst components metered in and an alteration in the activities of the catalyst components cannot be detected here.

The use of the density and $^1$H-NMR spectroscopy for determining physical properties of polymers such as density, proportion of monomer, molecular weight, viscosity, etc., is disclosed in JP-A-09-071605. Here, the physical property is determined by multiregression analysis, e.g. principal component analysis, and used for regulating the polymerization process. However, only the physical parameters of the polymers are determined in this document. The determination of the polymer composition by means of NMR spectroscopy is not mentioned. Furthermore, multiregression analysis requires a considerable outlay in terms of calculation and corresponding hardware.

Figure 1:
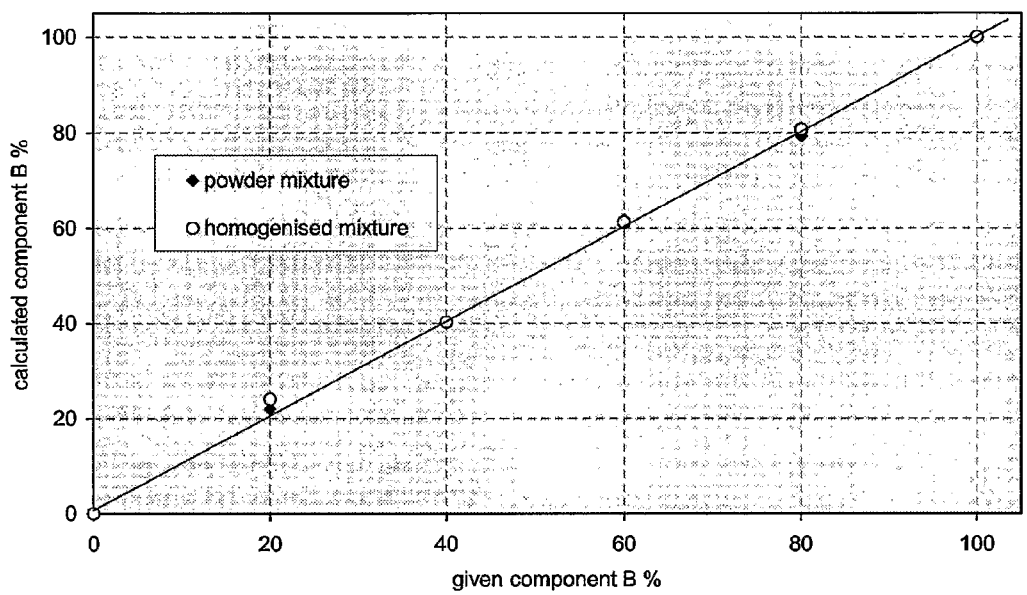
FIG. 1 illustrates a graph of calculated values of the proportion of component B for unhomogenized and homogenized samples versus the known proportion by weight of component B.

It was accordingly an object of the present invention to overcome the above-mentioned disadvantages of the prior art and to provide a method by means of which the composition of polymer mixtures can be determined quickly and simply. Furthermore, process integration for regulating the polymerization should be possible.

The invention is based on the surprising discovery that the proportions of the polymer components in polymer mixtures can be determined particularly quickly and simply by means of $^1$H-NMR spectroscopy.

The present invention accordingly provides a method of determining the composition of polymer mixtures comprising defined polymer components of differing mean molar masses $M_n$, which comprises the steps (a) recording of at least one $^1$H-NMR relaxation curve of the polymer mixture and (b) calculating the proportions of the polymer components by matching the measured relaxation curve with the relaxation curves of the individual polymer components.

According to the invention, a polymer mixture is any polymer product comprising at least two polymer components. For the purposes of the invention, the term "polymer component" refers to an ensemble of polymers which has a uniform distribution function of the molar masses, hereinafter referred to as the molar mass distribution for short. Such a uniform molar mass distribution can be produced, for example, under defined, essentially uniform physical and chemical polymerization conditions. The polymer components preferably have an essentially uniform number average of the molar masses $M_n$. It should be emphasized that although constancy of polymerization conditions over time during the polymerization is preferred, it is not necessary. Thus, for example, tube reactors can give a product which is uniform for the purposes of the invention even when the conditions in the reactor are not uniform; the same applies to batch operation of tank reactors. The applicability of the method of the invention is also independent of the width of the molar mass distribution or a particular distribution of the molar masses.

In the case of reactor cascades or multizone reactors, the polymer components correspond to the polymers which are formed in the respective cascade stages or reactor zones. The different number average molar masses $M_n$ can be achieved by varying the physical and also the chemical conditions. For example, a high molecular weight polymer component can be formed in one reactor with addition of small amounts of hydrogen and a low molecular weight polymer component can be prepared in a second reactor with addition of larger amounts of hydrogen. It is also possible, for example, to vary the comonomer content.

If, as is preferred, the polymerization is carried out in only a single reactor, for example a gas-phase fluidized-bed reactor, only variation of the chemical conditions in the polymer formation is available as differing process parameters, since targeted variation of the physical parameters for each polymer component is not possible. The term polymer component therefore preferably refers to a polymer which has been prepared by means of a specific type of active component in a polymerization catalyst consisting of a plurality of components. Particular preference is given to the use of a plurality of catalyst components which are immobilized together on a support.

According to the invention, at least two polymer components have to be present in the polymer mixture, but there is in principle no upper limit to the number of polymer components. However, the method is preferably applied to polymer mixtures having two, three, four or five polymer components, although it is also possible to employ polymer mixtures having a larger number of polymer components as long as these differ sufficiently in terms of their mean molar mass. The type of monomer or any comonomers present is of no significance for the polymer component.

Preference is given to the number average molar masses of the polymer components $M_n$ differing in each case by a factor of at least 1.3, preferably a factor of 1.5, particularly preferably a factor of 2. The larger the difference in the mean molar masses of the polymer components, the more precisely can the proportion of the respective polymer components be calculated.

Furthermore, it is preferred that the width of the molar mass distribution or the polydispersity of the polymer components $M_w/M_n$ is less than or equal to 10, preferably less than or equal to 8, particularly preferably less than or equal to 5. The additional use of polymer components having a relatively narrow polydispersity $M_w/M_n$ makes particularly precise calculation of the proportions of the polymer components possible. In general, a narrower molar mass distribution requires a smaller difference in the mean molar masses $M_n$.

For the purposes of the invention, physical conditions are all intensive and extensive physical parameters such as pressure, temperature, density, residence time, concentration or partial pressure of the reactants, concentrations or partial pressures of molar mass regulators, etc., which have any type of influence on the kinetics and/or thermodynamics of the polymerization reaction and thus on the composition of the polymer formed. Chemical conditions are, for the purposes of the present invention, the properties of the respective active site or sites of the catalyst or catalysts in respect of the chemical, i.e. molecular, properties of the polymer.

A prerequisite for the use of the method of the invention is that the spin-spin relaxation curves or times of the polymer components present in the polymer sample are known. These need to be determined before or after the measurement of the relaxation curves of the polymer mixture or in parallel thereto by means of measurements on the pure polymer components.

The methods of measuring $^1$H-NMR relaxation curves is generally known and are nowadays usually offered by the manufacturers of $^1$H-NMR instruments. All customary methods, for example the spin echo method or the FID (free induction decay) method, are equally suitable for the purposes of the present invention.

The measurement of the $^1$H-NMR relaxation curves can, for the purposes of the invention, be carried out on the melt or on the solid polymer powder or pelletized polymer, although the degree of crystallinity of the solid polymer should preferably be less than 5%. The measurement is preferably carried out on the melt or at a temperature only slightly below the melting point of the polymer mixture. The form of the sample can be varied within wide limits, so that processing of the samples prior to recording the $^1$H-NMR spectra can usually be omitted. Apart from films, compacts and other shaped polymer products, preference is therefore also given to using pellets, lumps, coarse powder or powder.

Possible polymers are in principle all polymers which display a dependence of the spin-spin relaxation time on the molar mass, in particular on the number average molar mass. These include, in particular, all polymers which contain C—C units derived from monomers having terminal C=C double bonds, regardless of the type of polymerization. The method is preferably applied to $C_2$-$C_{20}$-1-alkene or vinylaromatic homopolymers or copolymers, particularly preferably to a polyethylene or polypropylene homopolymer or copolymer. Monomers which can be used here are $C_2$-$C_{20}$-1-alkenes, in particular ethene, propene, 1-butene or 1-hexene, but the method can also be applied to other copolymers such as EPDM, EVA, etc. These can be either random copolymers or block or grafted copolymers. The method is particularly useful for HDPE, LDPE, LLDPE and copolymers thereof. The polymer components of the polymer mixture can be polymers of the same monomer, if appropriate with incorporation of comonomer, or else polymers of different monomers.

The method of the invention is preferably employed for determining the composition of polyolefins, in particular ethylene or propylene homopolymers or copolymers, without being restricted thereto. Surprisingly, it has also been found that the comonomer content of $C_3$-$C_{20}$-$\alpha$-olefins in polyethylenes, for example propene, butene, hexene or octene, has no significant influence on the determination of the composition. The method described is therefore also suitable for, for example, determining the composition of polymer mixtures comprising a low-comonomer low weight molecular weight polyethylene component and a comonomer-rich high molecular weight polyethylene component.

The proportions of the polymer components are calculated by matching the measured relaxation curve with the relaxation curves of the individual polymer components. Such matching is carried out using generally known mathematical methods, for example a least squares fit, regularization or the maximum entropy method.

It has surprisingly been found that the relaxation curves of the respective components $M_i(t)$ behave additively in proportion to the polymer component $m_i$ in the polymer mixture. The simplest and at the same time preferred method is therefore to make use of the fact that the curve of the polymer mixture M(t) is made up additively of the respective curves of the polymer components $M_i(t)$ $$M(t) = \sum_i m_i \cdot M_i(t), \text{ where } 1 = \sum_i m_i$$

The respective proportion of the polymer component is therefore given, for the example of a binary polymer mixture, by $$m_1 = \frac{M(t) - M_2(t)}{M_1(t) - M_2(t)}$$

This method can be employed both in the case of a homogenized sample and in the case of an unhomogenized sample. An advantage is that evaluation is possible even in the case of relaxation curves which are not simple exponential curves. However, a prerequisite for the use of this method is that the relaxation curves of both the polymer components and the mixture can be measured under identical instrumental conditions.

As an alternative, the spin-spin relaxation times $T^{ss}$ can be calculated from the relaxation curves of the individual components by fitting the mathematical parameters of a functional relationship to the measured curves. In the present case, a possible functional relationship is the exponential relationship $M(t)=A \exp -(t/\tau)^\beta$, where $\beta$ is usually equal to or less than 1. However, other functional relationships, for example polynomials, can in principle also be employed. From the spin-spin relaxation time of the polymer mixture $T^{ss}$ and the spin-spin relaxation times $T^{ss}_i$ of the individual polymer components ii, it is possible to calculate the mass fractions of the polymer components $m_i$ from the relationship $$\ln T^{ss} = \sum_i m_i \ln T^{ss}_i.$$

The quality of the calculation of the proportions of the polymer components is largely independent of the homogeneity of the polymer sample itself. It is therefore possible and preferred to carry out the measurement of the $^1$H-NMR relaxation curve of the polymer mixture (step a) on the unhomogenized polymer pellets or powder or on the unhomogenized polymer melt. Homogeneity has to be ensured only to such an extent that the sample is representative of the polymer mixture so that deviations between samples are avoided, while fluctuations in the pelletized polymer itself or on the millimeter scale in the melt do not adversely affect the applicability of the method.

The abovementioned method is particularly useful for the rapid determination of the composition of the polymer mixture in one or more polymerization reactors.

The invention therefore further provides a method of regulating the composition of a polymer mixture in at least one polymerization reactor in which at least two polymer components having differing mean molar masses $M_n$ are prepared sequentially or in parallel, which comprises the steps (a) recording of at least one $^1$H-NMR relaxation curve of the polymer mixture and (b) calculating the proportions of the polymer components by matching the measured relaxation curve with the relaxation curves of the individual polymer components (c) fitting at least one polymerization parameter (setting parameter) as a function of the actual proportions (actual value) and the required proportions (desired value) of the polymer components in the polymer mixture.

The regulating method can be used in all polymerization processes in which polymers comprising more than one polymer component are produced.

The sequential preparation of the polymer components can occur, for example, in a reactor cascade, preferably a cascade having from 2 to 5 reactors, or a multizone reactor, preferably a reactor having two reaction zones. The polymer components are in this case prepared sequentially by varying at least one polymerization parameter. Polymerization parameters which can be employed here are all the abovementioned physical and/or chemical parameters such as pressure, temperature, density, residence time, concentrations or partial pressures of the reactants, concentrations or partial pressures of molar mass regulators, etc. The only prerequisite is that the polymerization parameter has an influence on the composition of the polymer formed. However, it is also possible, particularly in cascades, to employ different catalyst components or catalysts in the different reactors, even if this is not necessary because of the physical separation of the polymerization reactions for the various polymer components.

The polymerization is preferably carried out in only a single reactor in which the polymer components are prepared in parallel by means of at least two catalyst components. The polymerization can be carried out in the single reactor in the gas phase, in the liquid monomer or in an inert liquid, for example in a saturated hydrocarbon, with the use of a gas-phase fluidized-bed reactor being preferred. If the polymerization is, as is preferred, carried out in only one polymerization reactor, the choice of polymerization parameters is restricted to parameters by means of which the polymerization behavior of a catalyst component can be influenced, ideally independently of the other catalyst components or else at least more strongly than that of the remaining catalyst components.

The substantial independence of the method of determination on the homogeneity of the sample makes it possible to use the method directly for determining the composition of the polymer powder in a particle-forming process, e.g. in the gas-phase fluidized-bed reactor or a suspension reactor, without further processing of the polymer powder being necessary. Products from a solution or high-pressure process can also be employed.

The matching of a polymerization parameter can be carried out manually or preferably automatically. The possibility of implementing such a method of determination in process regulation is generally known and can be achieved, for example, within the framework of an advanced process controller.

The polymerization parameter is preferably the amount fed into the reactor per unit time of at least one of the catalyst components which forms one of the respective polymer components in the reactor. It is in this case possible to alter only one catalyst component or a plurality of catalyst components in such a way that the actual value of the composition is influenced in the direction of the desired value. For example, the proportions of the catalyst streams having a different content of at least two catalyst components can be controlled in a simple manner as described in WO 00/50466. Alternatively, the major part of the catalyst mixture used can be kept constant and adjusted by means of one or more small streams of one or more catalyst components, as is described in WO 96/09328.

For the present purposes, a catalyst component is any polymerization-active substance or substance mixture which gives a polymer component according to the invention under the polymerization conditions. It is possible to use, in particular, all known catalysts such as Ziegler-Natta catalysts, Phillips catalysts and catalysts based on transition metal complexes with organic ligands. It is possible to use mixtures of the same type of catalysts or, preferably, mixtures of various types of catalysts, with there being no restriction to a particular type or combination of catalysts as long as they can be used in parallel in the reactor and produce different polymer components in the sense of the invention. Supported and unsupported catalyst components can be used.

Particularly useful catalysts are catalysts comprising at least two transition metal complexes, as described in the German patent application DE 10 2004 0205256.

An especially useful catalyst composition comprises at least two different polymerization catalysts of which at least one is a polymerization catalyst based on a monocyclopentadienyl complex of a metal of groups 4-6 of the Periodic Table of the Elements whose cyclopentadienyl system is substituted by an uncharged donor or is a hafnocene and at least one is a polymerization catalyst based on an iron component having a tridentate ligand which bears at least two ortho, ortho-disubstituted aryl radicals. Systems of this type are described in the German patent application DE 10 2004 0205248.

The control of one or more catalyst components as a function of the proportions of the polymer components is particularly simple when the amounts of the catalyst components correlate directly with the polymer components formed, i.e. there are no interactions between the various catalyst components. It is in this case possible to alter the polymerization parameter independently of the other catalyst components so that the desired value of the polymer composition is established. Otherwise, the dependences between the catalysts have to be determined and included in the regulation. In such a case, regulation using fuzzy logic systems by means of which complicated dependences can be incorporated, especially in the case of ternary or higher catalyst mixtures, is particularly advantageous. The use of regulation methods of this type in chemical processes is generally known.

Furthermore, the polymer mixture is preferably taken continuously or discontinuously from the polymerization reactor, melted if appropriate and subjected to the NMR measurement. Alternatively and likewise preferably, the polymer mixture is taken continuously or discontinuously from an apparatus for processing the polymer mixture installed downstream of the polymerization reactor, melted if appropriate and subjected to the NMR measurement. Apparatuses of this type installed downstream of the polymerization reactor are, in particular, extruders or kneaders.

The determination of the polymer composition can be carried out in-line, on-line or at-line. It is suitable both for cascade and multizone reactors and also, in particular, for a single-stage process using multicomponent catalysts. In cascade and multizone reactors, polymer can be taken from each reactor or each zone and passed to the NMR measurement.

To supplement the determination of the composition by means of $^1$H-NMR spectroscopy, it is also possible to incorporate other methods of determination, e.g. gel permeation chromatography, into the regulation of the polymerization process. The same also applies to the determination of further properties of the polymer, e.g. the rheological behavior, molecular or mechanistic properties.

Finally, the present invention provides a process for the polymerization of olefins in at least one, preferably only one, polymerization reactor using the abovementioned methods of determination and/or regulation. The polymerization process is preferably carried out in a gas-phase fluidized-bed reactor as is described in detail in, for example, EP-A-0 475 603, EP-A-0 089 691 or EP-A-0 571 826.

The polymerization process is preferably a continuous process for the polymerization of olefins in at least one polymerization reactor to form a polymer mixture comprising at least two polymer components, in which the fluid monomeric component and also, if appropriate, one or more comonomers is/are polymerized under the reaction conditions in the presence of a catalyst comprising one or more catalyst components, with the polymer mixture formed being taken off continuously or discontinuously. Here, (a) at least one $^1$H-NMR relaxation curve of the polymer mixture is measured, (b) the actual proportions of the polymer components are calculated by matching the measured relaxation curve with the relaxation curves of the individual polymer components and (c) altering at least one polymerization parameter as a function of the actual proportions and the required proportions of the polymer components in the polymer mixture.

The polymerization process is particularly preferably a process for the polymerization of ethylene in a gas-phase fluidized-bed reactor to form a polymer mixture comprising two or three polymer components, in which ethylene or ethylene together with one or more comonomers is polymerized under reaction conditions in the presence of a catalyst comprising two or three catalyst components in the polymerization zone of (precisely) one fluidized-bed reactor, with the polymer mixture formed being taken off continuously or discontinuously. Here, (a) at least one $^1$H-NMR relaxation curve of the polymer mixture is measured, (b) the actual proportions of the polymer components are calculated by matching the measured relaxation curve with the relaxation curves of the individual polymer components and (c) altering the amount or the reactivity of at least one of the catalyst components as a function of the actual proportions and the required proportions of the polymer components in the polymer mixture.

In a further process according to the invention for the polymerization of olefins in which a polymer mixture comprising at least two polymer components is prepared in at least one polymerization reactor, the ratio of the polymer components in the polymer mixture is determined by means of $^1$H-NMR spectroscopy. It is preferred that the polymerization is carried out in only one polymerization reactor using at least two catalyst components which produce at least two polymer components.

In general, a gas-phase fluidized-bed reactor is a more or less long, vertical tube through which circulated reactor gas flows. In general, the circulated reactor gas is fed in at the lower end of the gas-phase fluidized-bed reactor and taken off again at its upper end. When the reactor is used for the polymerization of α-olefins, the circulated reactor gas is usually a mixture of ethene or propene, if desired a molecular weight regulator such as hydrogen and inert gases such as nitrogen and/or saturated hydrocarbons such as ethane, propane, butane, pentane or hexane. In addition, the reactor gas can further comprise $C_3$-$C_8$-α-olefins such as propene, 1-butene, 1-pentene, 2-α-monoolefins such as propene, 1-butene, 1-pentene, 2-methylpentene, 1-hexene, 1-heptene and 1-octene as comonomers. Preference is given to a process in which ethylene is copolymerized with 1-hexene or 1-butene. The velocity of the reactor gas has to be sufficiently high, firstly, to fluidize the mixed bed of finely divided polymer which is present in the tube and serves as polymerization zone and, secondly, to remove the heat of polymerization effectively.

To set constant reaction conditions, the constituents of the reactor gas can be fed directly into the gas-phase fluidized-bed reactor or be fed in via the circulated reactor gas.

Furthermore, the amount of catalyst metered in determines the product output of the gas-phase fluidized-bed reactor. Its capacity is, as is known, limited by the cooling capacity of the circulated reactor gas. This cooling capacity depends, firstly, on the pressure of the reactor gas or at which the (co)polymerization is carried out. It is generally advisable to work at pressures of from 0.1 to 10 MPa, preferably from 0.5 to 8 MPa and in particular from 1.0 to 3 MPa. In addition, the cooling capacity depends on the temperature at which the (co)polymerization in the fluidized bed is carried out. The process is advantageously carried out at temperatures of from 30 to 160° C., particularly preferably from 65 to 125° C., where temperatures in the upper part of this range preferably being set for copolymers of relatively high density and temperatures in the lower part of this range preferably being set for copolymers of relatively low density.

The methods of determination are illustrated below with the aid of an example, without the invention being restricted thereto.

EXAMPLE

Mixtures of two polymer components A and B were prepared in each case.

spectrometer (Bruker Minispec mq 20 NMR analyzer) and electronically stored. The relaxation times were calculated from the relaxation curves in accordance with $M(t)=A \exp -(t/\tau)^\beta$ by a nonlinear least squares fit.

The relaxation curves of the polymer mixtures were subsequently measured under identical conditions. The proportions of the polymer components were determined by assumption of additive behavior of the relaxation curves of the polymer components, as described above or a two-component mixture. The calculated values of the proportions by weight $m_B$ of the component B for the purely physical mixtures are shown in the left-hand part of Table 1, and the values for the homogenized samples are shown in the right-hand part of Table 1.

The calculated values for the proportions of the polymer component B in the unhomogenized and the homogenized samples are plotted in FIG. 1 against the known proportion by weight of the component B. It can clearly be seen that the method is very useful for determining the composition of polymer mixtures. The values lie on a straight line. No significant deviations between the homogenized and the unhomogenized sample can be observed.

Figure 2:
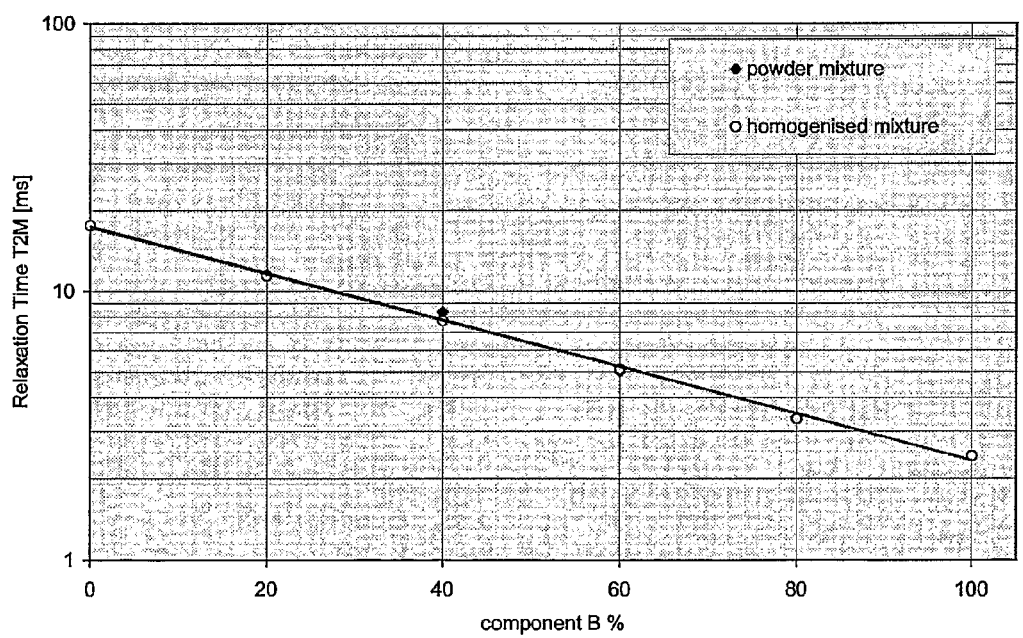
FIG. 2 illustrates a graph of spin-spin relaxation times $T^{ss}$ of samples versus the proportion by weight $m_B$ of component B.

The same applies to the spin-spin relaxation times $T^{ss}$ of the samples plotted against the proportion by weight $m_B$ of the component B in FIG. 2. The values likewise lie on a straight line. No significant deviations between the homogenized and the unhomogenized sample can be observed.

TABLE 1

| Proportion of B | Physical mixture | | | Homogenized mixture | | |
|---|---|---|---|---|---|---|
| [% by wt.] | Sample | $m_B$ [% by wt.] | $T^{ss}$ [ms] | Sample | $m_B$ [% by wt.] | $T^{ss}$ [ms] |
| 0 | 01b | 0.0 | 17.6 | 01b | 0.0 | 17.6 |
| 20 | 10b | 22.0 | 11.5 | 06b | 24.1 | 11.4 |
| 40 | 09b | 40.0 | 8.3 | 17y | 40.3 | 7.8 |
| 60 | 07b | 61.8 | 5.0 | 04b | 61.2 | 5.1 |
| 80 | 08b | 79.3 | 3.4 | 03b | 80.7 | 3.3 |
| 100 | 02b | 100.0 | 2.4 | 02b | 100.0 | 2.4 |

The component A was a high density polyethylene (HDPE) having a number average molar mass $M_n$ of 15 324, determined by gel permeation chromatography, and a polydispersity $M_w/M_n$ of 3.2. The component B was high density polyethylene (HDPE) having a number average molar mass $M_n$ of 83 157 g/mol and a polydispersity $M_w/M_n$ of 3.6. The components were ethylene homopolymers in powder form.

Firstly, purely physical polymer mixtures of the two polymer components A and B were produced. For this purpose, the proportions of powders were weighed out and mixed by shaking.

Secondly, a homogenized polymer mixture of the two polymer components A and B was prepared by dissolving the physically mixed polymer samples in xylene (2% strength solution, about 30 min) under reflux. The solution was then poured into ice-cold acetone and precipitated. The precipitate was separated off from the acetone by filtration, washed with acetone and then dried at about 60° C. and 0.01 Pa in a vacuum drying oven.

Firstly, the spin-spin relaxation curves of the components A and B were measured at 140° C. For this purpose, a sample of the respective polymer components was heated to 140° C. and the relaxation curves were recorded using a $^1$H-NMR

The invention claimed is:

1. A method of determining the composition of a multimodal polyolefin mixture comprising at least two defined polymer components having relaxation curves and differing number average molar masses $M_n$, comprising:
    (a) polymerizing olefins in at least one polymerization reactor, thereby forming a multimodal polyolefin mixture comprising at least two polymer components;
    (b) recording at least one $^1$H-NMR relaxation curve of the polyolefin mixture;
    (c) preparing samples of the pure polymer components of the polymer mixture before or after the measurement of the relaxation curves of the polymer mixture;
    (d) recording at least one $^1$H-NMR relaxation curve for each of the polymer components of the polyolefin mixture; and
    (e) calculating proportions of the polymer components by matching the relaxation curve of the polyolefin mixture measured in step (b) with the relaxation curves of the individual polymer components measured in step (d).

2. A method of regulating a composition of a multimodal polyolefin mixture in at least one polymerization reactor, the composition comprising at least two polymer components prepared sequentially or in parallel and having relaxation curves and differing mean molar masses $M_n$, comprising:

(a) polymerizing olefins in at least one polymerization reactor, thereby forming a multimodal polyolefin mixture comprising at least two polymer components;

(b) recording at least one $^1$H-NMR relaxation curve of the polyolefin mixture;

(c) preparing samples of the pure polymer components of the polymer mixture before or after the measurement of the relaxation curves of the polymer mixture;

(d) recording at east one $^1$H-NMR relaxation curve for each of the polymer components of the polyolefin mixture; and (e) calculating proportions of the polymer components by matching the relaxation curve of the polyolefin mixture measured in step (b) with the relaxation curves of the individual polymer components in step (d); and (f) fitting at least one polymerization parameter as a function of actual proportions and required proportions of the polymer components in the polyolefin mixture.

3. The method according to claim 1, wherein the composition of the polyolefin mixture is a composition in a polymerization reactor.

4. The method according to claim 1, wherein the recording of at least one $^1$H-NMR relaxation curve of the polyolefin mixture is carried out on unhomogenized polymer pellets or on an unhomogenized polymer melt.

5. The method according to claim 4, wherein the recording of the at least one $^1$H-NMR relaxation curve is carried out on the polymer melt.

6. The method according to claim 1, further comprising a molar mass distribution of the polymer components, $M_w/M_n$, less than or equal to 10.

7. The method according to claim 1, wherein the number average molar masses of the polymer components $M_n$ in each case differ by a factor of at least 1.3.

8. The method according to claim 1, wherein the matching of the measured relaxation curve of the polyolefin mixture with the relaxation curves of the individual polyolefin components is carried out by fitting mass fractions $M_i$ of the polyolefin components i to a relationship:

$$M(t) = \sum_i m_i \cdot M_i(t),$$

where M (t) is the relative magnetization of the polymer mixture as a function of time; $M_i(t)$ is the relative magnetization of the polymer component i as a function of time; and $m_i$ is the mass fraction of the polymer component i in the polymer mixture.

9. The method according to claim 1, wherein the matching of the measured relaxation curve of the polyolefin mixture with the relaxation curves of the individual polymer components is carried out by i) determining a spin-spin relaxation time $T_{SS\ i}$ from the relaxation curve of each polymer component;

ii) calculating a mass fraction $m_i$ of each polymer component i, with the mass fractions $m_i$ of the polymer components i being fitted to a relationship:

$$\ln T^{ss} = \sum_i m_i \ln T_i^{ss},$$

where $T^{ss}$ is the spin-spin relaxation time of the polymer mixture; $T^{ss}_i$ is the spin-spin relaxation time of the polymer component i; and $m_i$ is the mass fraction of the polymer component i in the polymer mixture.

10. The method according to claim 2, wherein the at least one polymerization reactor is a reactor cascade having from 2 to 5 reactors or a multizone reactor wherein the polymer components are prepared sequentially by varying at least one polymerization parameter.

11. The method according to claim 2, wherein the polymer components are prepared in parallel in one polymerization reactor with at least two catalyst components.

12. The method according to claim 11, wherein the polymerization reactor is a gas-phase fluidized-bed reactor.

13. The method according to claim 11, wherein the polymerization reactor is a suspension reactor.

14. The method according to claim 11, wherein the at least one polymerization parameter is an amount of at least one of the catalyst components fed into the polymerization reactor per unit time.

15. The method according to claim 3, wherein the polyolefin mixture is taken continuously or discontinuously from the polymerization reactor, and optionally melted.

16. The method according to claim 3, wherein the polymer mixture is taken continuously or discontinuously from an apparatus for processing the polymer mixture downstream of the polymerization reactor, and optionally melted.

17. The method according to claim 16, wherein the apparatus is an extruder.

18. A process comprising:

(a) polymerizing olefins in at least one polymerization reactor, thereby forming a multimodal polyolefin mixture comprising at least two defined polymer components having relaxation curves and differing number average molar masses $M_n$;

(b) recording at least one $^1$H-NMR relaxation curve of the polyolefin mixture;

(c) preparing samples of the pure polymer components of the polymer mixture before or after the measurement of the relaxation curves of the polymer mixture;

(d) recording at least one $^1$H-NMR relaxation curve for each of the polymer components of the polyolefin mixture; and (e) calculating proportions of the polymer components by matching the relaxation curve of the polyolefin mixture measured in step (b) with the relaxation curves of the individual polymer components measured in step (d).

* * * * *